United States Patent [19]
Berger et al.

[11] Patent Number: 6,013,033
[45] Date of Patent: Jan. 11, 2000

[54] INTRACAVITARY ECHOGRAPHIC IMAGING CATHETER

[75] Inventors: Genevieve Berger, Bourg la Reine; Nicolas Bovo, Arnouville; Isabelle Dufour, Bagneux; Jean-Paul Grandchamp, Gif sur Yvette; Pascal Laugier, Paris; Charles Sol, Wissous; Sylvain Allano, Montlhery, all of France

[73] Assignee: Centre National de la Recherche Scientifique

[21] Appl. No.: 08/894,213

[22] PCT Filed: Jan. 30, 1996

[86] PCT No.: PCT/FR96/00155

§ 371 Date: Aug. 31, 1998

§ 102(e) Date: Aug. 31, 1998

[87] PCT Pub. No.: WO96/23444

PCT Pub. Date: Aug. 8, 1996

[30] Foreign Application Priority Data

Feb. 1, 1995 [FR] France ................... 95 01173

[51] Int. Cl.[7] .......................................... A61B 8/12

[52] U.S. Cl. .............................................. 600/466; 600/472

[58] Field of Search ..................... 600/462, 463, 600/459, 466, 472; 29/25.35

[56] References Cited

U.S. PATENT DOCUMENTS

| | | | |
|---|---|---|---|
| 5,367,878 | 11/1994 | Muntz et al. | 60/512 |
| 5,606,975 | 3/1997 | Liang et al. | 600/463 |
| 5,779,643 | 7/1998 | Lum et al. | 600/462 |

*Primary Examiner*—Francis J. Jaworski
*Attorney, Agent, or Firm*—Omri M. Behr, Esq.

[57] ABSTRACT

Catheter for echographic imaging within a cavity, comprising a proximal end situated to the outside of the patient, a distal end situated close to the tissues which are to be investigated, and a body connecting these two ends, the distal end comprising a guide wire and a capsule which is transparent to ultrasound and in which are accommodated a fixed piezoelectric transducer and a mirror for deflecting the ultrasonic wave and driven by means of rotation accommodated in the said capsule, this catheter being characterized in that the said mirror (30) is placed directly, without torque transmission shaft, on the surface of the rotor (34) of a microactuator constituting the said means of rotation.

17 Claims, 2 Drawing Sheets

INTRACAVITARY ECHOGRAPHIC IMAGING CATHETER

FIELD OF THE INVENTION

The present invention relates to a catheter for echographic imaging within a cavity.

BACKGROUND

It is known that the detection and the evaluation of the severity of certain diseases are based on the analysis of echographic images. Thus, intravascular ultrasound imaging has been developed for characterizing atheromatous lesions in man. The resolution which can be obtained with ultrasound depends in fact on the frequency used, and the higher this frequency, the better the resolution. However, the attenuation which the ultrasound beam suffers increases with the frequency, and the depth of penetration of the beam diminishes considerably. An image with very good resolution at high frequency can therefore only be obtained by the intravascular route.

The treatment of the lesions due to the presence of atheromatous plaque in the coronary arteries involves recourse to two distinct invasive techniques: surgery and catheter intervention (balloon angioplasty or laser). The use of catheterized instruments represents a comfortable alternative. However, surgery proves necessary when the lesions are serious, that is to say when they are in an advanced state. In this case, the surgical interventions consist in replacing the stenosed portion of the coronary artery with part of another artery, either by removal and grafting, which creates a bypass round the zone, or by using another artery to irrigate the heart.

The catheters are used for the interventions employing the balloon angioplasty technique. In this technique, a catheter measuring about 1.5 meters in length and 1 mm in diameter is introduced percutaneously into the femoral artery and is advanced to the coronary artery by progressing through the arterial network. The probe is guided with the aid of a guide wire which may or may not be integral with the catheter and whose end is curved in order to avoid perforations during the manoeuvres needed for advancing and orienting the catheter. This progress is monitored by an external imaging technique, which makes the positioning easier and safer. The therapy can also be based on the abrasion of the atheromatous plaque by laser or mini-scalpel, the guiding of which is based on the same principle as for the angioplasty catheters.

The criteria for the choice of using one or other of the methods mentioned hereinabove are empirical. They take account of a priori knowledge of the structure of the plaque and of the extent of its thickness and length. Despite the preference for angioplasty, because of its greater simplicity, the two methods nevertheless entail substantial risks.

The manoeuvrability of the catheter, the simplification of the intervention procedures, the increase in the resolution cell and the awareness of the position of the distal end of the catheter are the key points in the development of this therapeutic control technique.

Intracoronary echography is distinguished by the small dimensions of the elements to be investigated and of the routes for gaining access to these. This is reflected in a quite particular specification for the design of the catheters, the piezoelectric elements, the elements permitting scanning, and the instruments for treating the stenoses.

Furthermore, the aim of quantitative echography is the complete exploitation of the echographic signal and the extraction of the quantitative parameters aiding in the diagnosis and providing additional information compared to the traditional echographic image. Thus, the methods for characterizing tissues by ultrasound permit estimation of the quantitative parameters on the basis of the echographic signal or echographic image. These methods also demand specific characteristics as regards the systems for obtaining the echographic signals or images.

Thus, the cable of the catheter, the total length of which is about 1.50 meters, has a proximal part which is sufficiently rigid to permit guiding, and a more flexible distal part which has an overall diameter of 1 to 2 mm and a length of 2 to 15 cm. The distal end is made up of a capsule which is transparent to ultrasound and which contains the echographic system immersed in a coupling liquid. The assembly must be compatible with the biological media, and polymers such as silicone, polyvinylchloride, polyethylene, polyurethanes, polyesters, polytetrafluoroethylene, are generally used for its production.

The central frequency of the wide-band transducers used varies from 20 to 40 MHz and their supply voltage is between 100 and 300 V.

The catheterized ultrasound probes used for intracoronary echography can be classified in two ways: according to the mode of scanning permitting construction of the image, and according to the treatment instruments installed in the catheter.

The first solution for constructing an image in a sectional plane consists in making the piezoelectric element turn. The principal characteristic of this solution lies in the need to have electric contacts between a mobile part, consisting of the transducer, and a fixed part, consisting of the external medium. Moreover, the distance separating the ultrasound source from the tissues to be investigated is small, hence the risk of positioning in the near-field zone. To solve the latter problem, use is made of a rotating mirror, either plane or concave, which deflects the ultrasonic waves through 45°, and this makes it possible, by means of the transducer emitting in the axis of the catheter, to lengthen the distance between the emitter and the tissues. Whilst maintaining this structure, the transducer can be fixed to the catheter, with the mirror being the only installed element.

This latter solution is the one most commonly used. However, the mobile assembly consisting of a transducer and of a mirror is used for positioning the catheter after an independent guide wire has been introduced.

To illustrate the state of the art in this field, the following may be mentioned in particular:

U.S. Pat. No. 4,794,931, which describes a catheter for echography within a cavity, the distal end of which is equipped with an ultrasound transducer, this transducer being able to be driven in rotation by an external motor in order to guarantee the scanning by the beam.

WO 93/05712, which also describes a catheter for echography within a cavity, the distal end of which includes a fixed ultrasound transducer, a mirror for deflecting the ultrasonic waves and oriented at 45°, and a micromotor which is of the timepiece type and on whose shaft the said mirror is mounted by a posteriori assembly.

The systems currently known for catheterized echography have the following faults in particular:

the length of the catheter and the passage of the latter through cavities of curved geometry generating a variable torque, there is no control of the angular position or speed of rotation of the distal end of the catheter, and hence of the member for emission and acquisition of the ultrasonic waves, the variations in the speed of rotation cause distortion of the image, the catheter conveys a mechanical shaft whose rigidity is inimical to mobility through the sinuous arterial network, additionally presenting the risk of dissection of the atheromatous plaque, the large diameter of the distal end of the catheter permits only a reduced investigation of the coronary arteries, limited to the proximal zones, where the stenosis does not greatly reduce the lumen of the vessel, the lack of manoeuvrability of the mechanical scanning devices due to the connection to an external rotation module, the rigidity of the distal end of the catheters motorized internally, due to the substantial length of the micromotor and of its shaft (greater than 5 mm); this part not being flexible and rendering the positioning of the catheter dangerous (perforation, detachment of atheromatous plaque), the use of a micromotor of the electromagnetic type requires double electromagnetic compatibility with the biological environment and the distal capsule of the catheter: both for the electric field and for the magnetic field.

SUMMARY

Starting from this prior art, the invention proposes to make available a catheter for echographic imaging within a cavity, which is of small size and does not have the disadvantages of this prior art.

To this end, the catheter according to the invention is of the type which includes a proximal end situated to the outside of the patient, a distal end situated close to the tissues which are to be investigated, and a body connecting these two ends, the distal end comprising a guide wire and a capsule which is transparent to ultrasound and in which are accommodated a fixed piezoelectric transducer and a mirror for deflecting the ultrasonic wave and driven by means of rotation accommodated in the said capsule, this catheter being characterized in that the said mirror is placed directly, without torque transmission shaft, on the surface of the rotor of a microactuator constituting the said means of rotation.

According to the invention, the microactuator is an electrostatic motor fabricated using collective fabrication procedures, without assembly, derived from the procedures used in microelectronics (silicon technology) and/or by specific procedures for the production of three-dimensional micro-objects, especially by electroforming. This electrostatic motor is preferably of variable capacitance and radial excitation.

According to one characteristic of the invention, the external diameter of the said microactuator is between 0.1 mm and 1 mm, typically 0.5 mm, and its thickness is between 10 and 100 µm.

According to one preferred embodiment of the invention, the mirror is made up of a plate of high acoustic impedance compared to the liquid inside the capsule, oriented at about 45° in relation to the axis of the transducer, the said plate being situated at the top of a cylinder cut at about 45° and turning in the axis of the probe. According to one illustrative embodiment, this plate can be metal.

According to one preferred embodiment by means of which it is possible to eliminate the unbalance resulting from the fact that the centre of gravity of the cylinder, at the top of which the said plate is placed, is not situated on the axis of rotation, the said mirror is made in the form of a disc placed on a support leg connected directly to the rotor of the microactuator. This disc, which can have a concave or plane shape, includes a fine reflecting layer, for example of metal, deposited on a medium which absorbs ultrasound.

Other characteristics and advantages of the present invention will be evident from the following description which is given with reference to the attached drawings, in which:

DETAILED DESCRIPTION OF THE INVENTION

Figure 1:
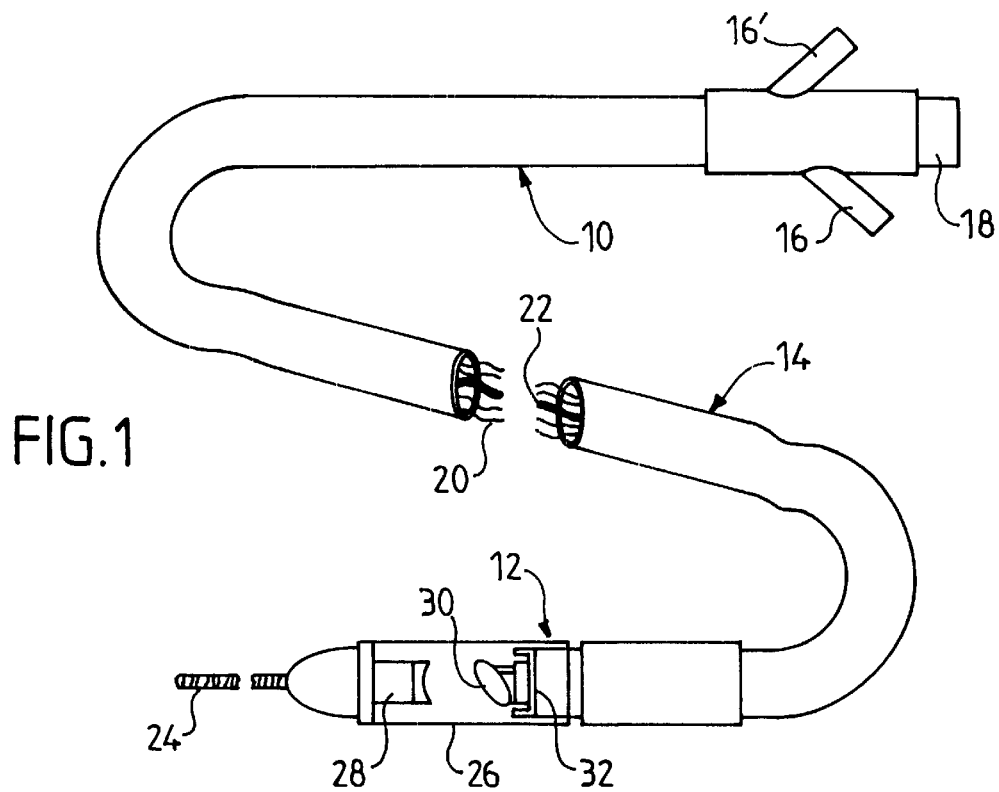
FIG. 1 is a diagrammatic elevation view of an illustrative embodiment of a catheter equipped with a probe with micromotor according to the present invention.

As can be seen in FIG. 1, the catheter according to the invention for echographic imaging within a cavity comprises a proximal end 10 situated to the outside of the patient, a distal end 12 situated close to the tissues which are to be investigated, and a body 14 connecting these two ends.

The proximal end 10 is equipped with the electric connections for the means rotating the mirror which is placed in the capsule at the distal end 12, the electric connections for the piezoelectric transducer, also placed in this distal end, and the junction interfaces between the treatment instrument and its external control device (laser, balloon angioplasty, or dissection scalpel). In FIG. 1, the conduits 16, 16' and 18 which are provided for the passages of these different cables are shown schematically.

The body 14 of the catheter is the connecting member between the active part (described hereinafter), situated at the distal end 12, and the command, acquisition and control system situated to the outside of the patient. This body contains the electric cables 20 for powering the means driving the mirror (described hereinafter) and the piezoelectric transducer, the supports conveying the command signals for the treatment instrument, the passages for fluids 22, etc.

The distal end 12 essentially comprises the guide wire 24 and the capsule 26 which is transparent to ultrasound and in which is positioned the device for spatial echographic acquisition of planes or sections. The therapeutic treatment instrument is situated to the rear of this capsule. The device for echographic acquisition is made up of a fixed piezoelectric transducer 28, plane or focused, and of a mirror 30 for deflecting the ultra-sonic waves, which is preferably oriented at an angle of 45°, driven in rotation.

The image is constructed, in a known manner, by the scanning of the ultrasonic wave at the distal end 12 of the catheter. For this purpose, according to the invention, the acquisition device placed in the capsule 26 includes the fixed axial piezoelectric transducer 28, plane or focused, and the mirror 30 providing for the deflection of the ultrasonic wave, this mirror being driven in rotation by a rotating machine 32. The direction of the catheter and that of the vector of the wave emitted by the transducer 28 are co-linear but in opposite directions. According to one preferred embodiment of the invention, the rotating machine 32, incorporated in the distal end of the catheter, is made up of an electrostatic rotary microactuator which is fabricated using collective fabrication procedures derived from the procedures used in microelectronics. For certain applications in which the problems of electromagnetic compatibility do not apply, an electromagnetic rotary microactuator may be produced, also fabricated using collective fabrication procedures.

Figure 2:
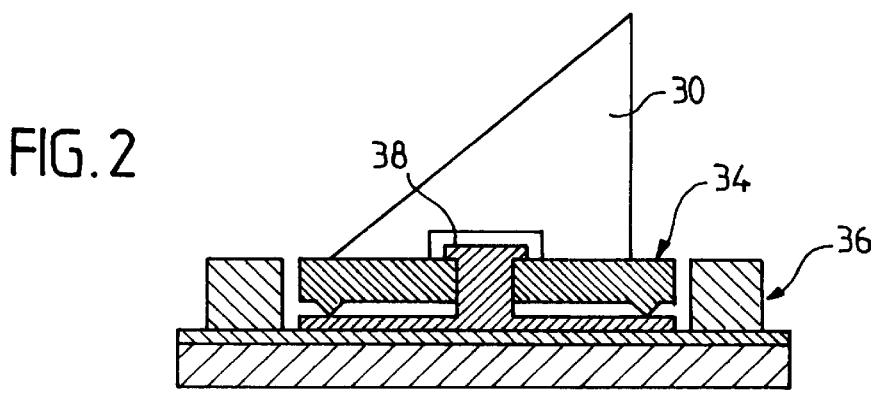
FIG. 2 is an elevation view of a detail of the probe, represented on a larger scale, this detail being made up of the mirror/rotor system of the micromotor.

As can be seen in FIG. 2, the mirror 30 is placed directly on the surface of the rotor 34 of the electrostatic micromotor 32. By means of this arrangement, the mirror 30 is not driven by the motor shaft: there is no transmission of rotation to the shaft 38, the latter is fixed and serves only as a centring and locking means, given that the motor 32 has to function in any position.

Figure 6:
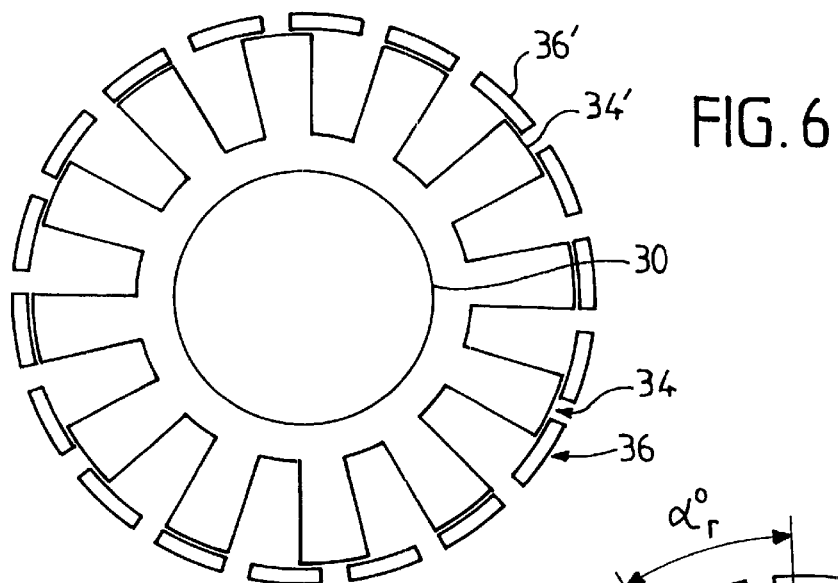
FIG. 6 is a plan view of an illustrative embodiment of the motor/mirror micro-system.
Figure 7:
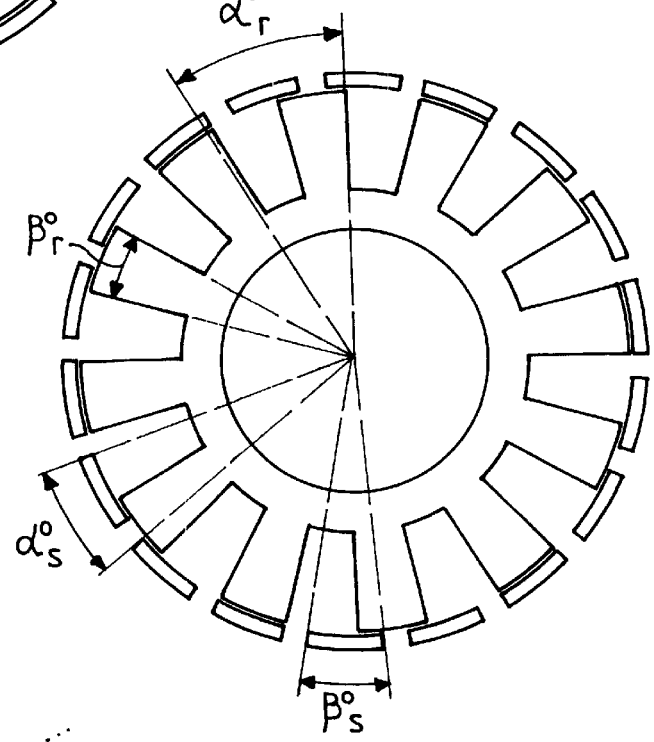
FIG. 7 is a view similar to FIG. 6, indicating the definitions of the rotor and stator angles of the micromotor.

The electrostatic motor 32 is preferably of variable capacitance and radial excitation. Its external diameter is between 0.1 and 1 mm, typically 0.5 mm, and its thickness is between 10 $\mu$m and 100 $\mu$m. The space between the stator 36 and the rotor 34 is between 1 and 7 $\mu$m. The geometric structure of the motor (FIGS. 6 and 7) is preferably of the 3/2 type (that is to say it includes 3p stator pins 36' and 2p rotor teeth 34', p being an integer). The dimensioning of the stator pins 36' and of the rotor teeth 34' is such that:

$\beta_r \in [0.3;07]$ and $\beta_s \in [0.4;0.9]$, with typically $\beta_r=0.5$ and $\beta_s=0.75$.

If Nr is the number of rotor teeth and Ns the number of stator pins, this gives (FIG. 7):

$$\alpha^o_r = 2\pi/Nr, \ \alpha^o_s = 2\pi/Ns$$

$$\beta_r = \beta^o_r/\alpha^o_r, \beta_s = \beta^o_s/\alpha^o_s$$

The materials used for the stator and the rotor are silicon or materials (pure or in alloy form) and polymers.

The microsystem contained in the capsule 26 is immersed in an intracapsular liquid, providing for ultrasound coupling. This liquid must have low viscosity, be nonconducting and cause little attenuation, with, if possible, a high electric permittivity. It is possible, for example, to use deionized water or oils.

By designing a microsystem consisting of a fixed transducer 28 and of a rotating ultrasound reflector 30, it is possible to lengthen the distance between these two elements. Because of the closeness of the probe and of the tissues which are to be investigated, it is in fact necessary to increase the distance between this probe and these tissues in order to overcome the problems associated with the near-field zone. In this case, the connections of the transducer are fixed, which eliminates any rotating connection.

Figure 3:
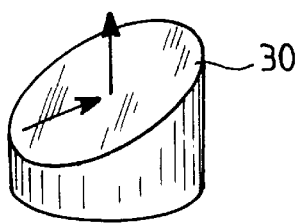
FIG. 3 is a diagrammatic perspective representation of an illustrative embodiment of a mirror which can be used in the said catheterized probe.

According to one embodiment of the invention, the mirror 30 can be made in the shape (FIG. 3) of a plate, preferably of metal, with high acoustic impedance and oriented at about 45° in relation to the axis of the transducer 28, this plate being placed at the top of a cylinder cut at about 45° and driven in rotation according to the axis of the probe. This solution has the disadvantage, however, that the centre of gravity of the cylinder is not situated on the axis of rotation, which creates a problem of unbalance. The latter can be compensated, for example, by adding a dead weight in order to balance the structure. Moreover, the height of such a cylindrical structure does not favour its technological production in conjunction with the micromotor 32. Separate construction, followed by assembly, would considerably increase the cost of the system as a whole.

The reduction in the height of the cylinder and the equilibrium of this structure are the two major restrictions dictating the choices leading to other solutions according to the invention.

The unbalance caused by the offset existing between the shaft of the motor 32 and its parallel passing through the centre of gravity of the cylinder bearing the mirror is eliminated by the alignment of these two straight lines. This solution is conceivable insofar as the possible underlying increase in the diameter of the assembly allows the specifications to be respected.

Figure 4:
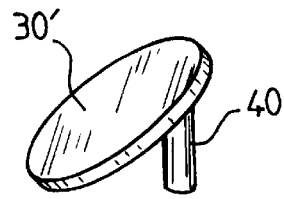
FIGS. 4 and 5 are diagrammatic views, in perspective and in cross-section, respectively, of another illustrative embodiment of the said mirror.
Figure 5:
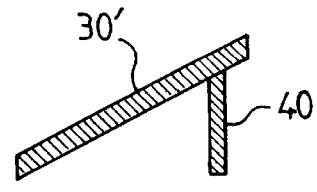

To reduce the weight of the mirror, the latter can be made in the form of a mirror disc 30', of high acoustic impedance, placed on a support leg 40 which is connected directly to the rotor 34 of the micromotor. This embodiment is illustrated in FIGS. 4 and 5.

It should also be noted that by inclining the elements of the mirror through an angle of less than 45°, it is possible to reduce the height of its supporting cylinder. With an angle of 30°, the height is practically halved.

According to the invention, the mirror is made up of a fine reflecting layer, preferably of metal, which is deposited on a medium which absorbs ultrasound. The mirror can be plane, but the beam reflected by the said mirror can be focused by giving it a concave shape, which additionally increases the resolution of the system.

Figure 8:
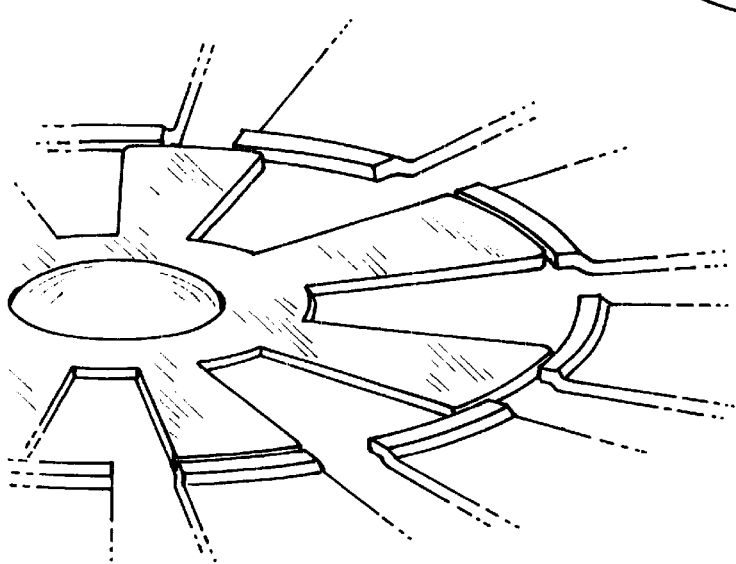
FIG. 8 illustrates, in a perspective view, a micromotor structure made of copper, produced by electro-forming, which can be used according to the invention.

According to the invention, the mirror is fabricated directly on the rotor of the micromotor by collective fabrication procedures derived from the procedures used in microelectronics (silicon technology) and/or by specific procedures for producing three-dimensional micro-objects, especially by electroforming. FIG. 8 in the attached drawings illustrates the structure of a copper micromotor thus obtained by electroforming.

The reduction in the size of the mirror, without energy loss, is a problem which is mitigated by using a focused transducer; the size of the beam being smaller, it is possible to reduce the diameter of the said mirror. The principal factors regarding the dimensions are associated with the possibilities of investigating the tissues (depth of investigated tissue, resolution) limited by the attenuation of the signals in the coupling liquid, in the blood and in the tissues.

As will be understood from the preceding description, the assembly consisting of the piezoelectric transducer 28, the mirror 30 and the microactuator 32 permitting the rotation of the mirror, constitutes the unit for ultrasound acquisition of the in vivo site of the catheter.

The positioning of this acquisition unit at the site is ensured by the guide wire 24 followed by the catheter. Once in place, the emission and reception of multiple echoes take place during the rotation of the mirror 30. The control of the motor 32, of the stepping type, permits precise positional information on the section thus formed. The axial displacements of the catheter and the acquisition of new sectional planes permit precise three-dimensional reconstruction and location of the stenoses which can be treated by the treatment unit situated at the distal end of the catheter, and proximal with respect to the ultrasound acquisition unit.

The advantages afforded by the invention are in particular the following:

Integration of the mirror system with the microactuator, with direct coupling of the mirror to the microactuator, without intermediate shaft, thereby producing an integrated "micromotor/mirror" microsystem.

Use of a microactuator and of a mirror which can be fabricated together, and without assembly, using a collective procedure.

Use of a lightweight mirror supported by a leg whose bearing zone does not cover the whole of the useful surface of this mirror;

Use of a mirror of low and constant thickness, which can have a rear damping medium;

Possibility of orienting the mirror by less than or equal to 45°;

Possibility of processing the information directly at the distal end of the catheter, and on the same silicon substrate as that used for the motor 32, by which means it is possible to produce a "mirror/motor/processing" microsystem of the ASIC type (Application-specific integrated circuit);

Miniaturizing the distal end of the catheter, thus making it possible to access the coronary arteries presenting a lumen with a diameter of less than 1 mm, typically 0.6 mm;

Reducing the rigid length of the distal end compared to the systems with a motor of the timepiece type placed at the end of the catheter;

Reducing the rigidity of the catheter, and particularly of its distal end, without adversely affecting the rotating characteristics of the scanning member, thereby making it possible not only to access vessel areas whose topography is particularly complicated, but also to reduce the risk of detaching fragments of atheromatous plaque in the arteries;

Controlling the speed of rotation of the micromotor and maintaining it at a constant value by means of dispensing with the mechanical transmission shaft between the motor and the mirror, responsible for the variable torque.

All these advantages permit:

A reduction in costs (equipment and examinations);

A precise approach to the topographical characteristics of the tissues observed; (awareness of the absolute position of the sensor in relation to the anatomical structure);

Superposing and readjusting images according to the exact information of the three-dimensional position of each of them, and joining with images from other imaging methods;

The extraction of quantitative acoustic parameters representative of the histological makeup of a precise zone. Various parameters make it possible to characterize the disease and evaluate its seriousness: thickness of the layers, speed of the ultrasounds, attenuation, coefficient of backscatter. Their representation in topographical form makes it possible to superpose these various parameters with the traditional images and the histological layers;

The three-dimensional reconstruction of an investigated volume by readjusting the various sections according to the precise information of the exact position of some in relation to the others; and The possibility of using the place which is freed by the absence of the mechanical transmission shaft for the displacement in the third dimension (longitudinal) of the microactuator, thereby permitting direct acquisition of a volume of images in three dimensions.

The main area of application of the invention is that of intravascular investigation of the coronary arteries. However, this application is not limiting, and indeed the device according to the invention can be used in the investigation of tissues which are not accessible by the intravascular route, particularly for percutaneous and in particular intra-articular investigation.

A particular solution for automatic piloting will now be discussed.

In order to obtain a constant speed of rotation, it is necessary to prevent the variations in motor torque. To do this, it is necessary to stop powering one stator pin, at the moment when a rotor tooth arrives in conjunction with the pin, and then to power the following stator pin. Such a control, called automatic pilot, is only possible if information is available concerning the position of the rotor. In practice it is not possible to place a position sensor on the micromotor. It is thus necessary to use the signals emanating directly from the micromotor to estimate the position of the rotor. As the capacitance between the rotor and a stator pin varies with the position of the rotor, it is possible to imagine ascertaining the position of the rotor by measuring this capacitance. In practice, the position measurement can thus be carried out by measuring the capacitance between non-powered stator pins and the rotor. The relative variation in this capacitance is very small (because the wires and the connections are the cause of a substantial mean capacitance) and a specific assembly is therefore proposed (amplifier ;with gain greater than 1 with a capacitance between the inlet and outlet) which, by a Miller effect, makes it possible to return an equivalent negative capacitance in parallel with the capacitance to be measured. Thus, the variations in capacitance (due to the movement of the rotor) are around a very low mean capacitance and the relative variation is therefore considerable and measurable (for example with the aid of an oscillator whose frequency depends on the capacitance, followed by a frequency demodulator).

For this type of automatic pilot control, the supply frequency no longer being controlled, the speed is regulated by acting on the value of the supply voltage.

Simulation results have demonstrated the validity of such automatic pilot control.

In order to determine the voltage necessary to obtain a uniform speed of rotation of 2000 rpm, simulations of this type of automatic pilot operation were carried out, assuming an initial speed of rotation of zero. By way of example, the simulation results when deionized water is used as coupling agent are indicated hereinbelow. For this example, the characteristics of the motor are Ns=30, Nr=20, r=229 =m (external radius of the rotor), e=3 $\mu$m (space between the rotor and the stator), hr=45 $\mu$m (height of rotor teeth), hs=20 $\mu$m (height of stator pins), 1=10 $\mu$m (thickness of motor), height of mirror=100 $\mu$m, and inclination of mirror=45°.

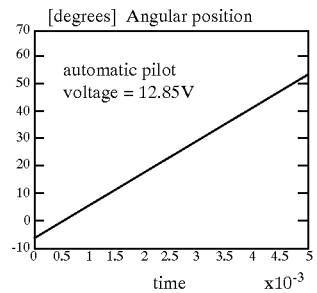

-continued

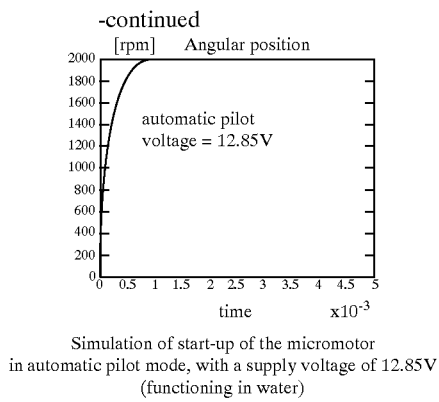

Simulation of start-up of the micromotor
in automatic pilot mode, with a supply voltage of 12.85V
(functioning in water)

We claim:

1. A intracavitary echographic imaging catheter including a proximal end adapted to be located outside the patient and a distal end situated adjacent to a tissue to be examined and a body linking said two ends, said distal end comprising a guide wire and an ultrasound transparent capsule housing a fixed piezoelectric transducer and an ultrasonic wave deflecting mirror driven by a rotating means in said capsule wherein, in said catheter the means for rotating comprise a microactuator having a stator and a rotor housed in said capsule, said mirror being arranged directly without the presence of a coupling transmission, on a surface of said rotor.

2. Catheter in accordance with claim 1 wherein the said microactuator is an electrostatic motor.

3. Catheter in accordance with claim 2 wherein said electrostatic motor has a variable capacity and radial excitation.

4. Catheter in accordance with claim 2 wherein the outside diameter of said motor is between 0.1 mm and 1 mm and said thickness is between 10 and 100 $\mu$m.

5. Catheter in accordance with claim 4 wherein the outside diameter of said motor is 0.5 mm.

6. Catheter in accordance with claim 1 wherein said microactuator is an electromagnetic motor.

7. Catheter in accordance with claim 1 wherein said mirror is directly attached to the rotor of the microactuator.

8. Catheter in accordance with claim 1 wherein said rotating mirror comprises a plaque of high acoustic impedance situated at the top of a cylinder cut to approximately 45° relative to the axis of the transducer and turning about the axis of the latter.

9. Catheter in accordance with claim 8 wherein said mirror is a thin reflecting layer placed on ultrasonically absorbent medium.

10. Catheter in accordance with claim 9 wherein said thin reflecting layer is metallic.

11. Catheter in accordance with claim 8 wherein said plaque is metallic.

12. Catheter in accordance with claim 1 wherein said mirror is in the form of a high acoustic impedance disc placed on a base directly contacted the rotor of said microactuator.

13. Catheter in accordance with claim 12 wherein said mirror is a thin reflecting layer placed on ultrasonically absorbent medium.

14. Catheter in accordance with claim 13 wherein said thin reflecting layer is metallic.

15. Catheter in accordance with claim 1 wherein said mirror is planar.

16. Catheter in accordance with claim 1 wherein said mirror is concave.

17. In the process of making a catheter according to claim 1, the step wherein the electrostatic motor is made by electroforming.

* * * * *